United States Patent [19]

Papenfuhs et al.

[11] Patent Number: 4,540,815
[45] Date of Patent: Sep. 10, 1985

[54] PROCESS FOR THE PREPARATION OF PURE 3-ACETYLAMINO-ANILINES

[75] Inventors: Theodor Papenfuhs, Frankfurt am Main; Manfred Hintzmann, Hofheim am Taunus, both of Fed. Rep. of Germany

[73] Assignee: Hoechst Aktiengesellschaft, Fed. Rep. of Germany

[21] Appl. No.: 672,400

[22] Filed: Nov. 16, 1984

[30] Foreign Application Priority Data

Nov. 19, 1983 [DE] Fed. Rep. of Germany ....... 3341883

[51] Int. Cl.$^3$ .................. C07C 102/00; C07C 102/04
[52] U.S. Cl. ..................................... 564/216; 564/218
[58] Field of Search ................................ 564/218, 216

[56]       References Cited
        U.S. PATENT DOCUMENTS 3,857,886 12/1974 Hewsel et al. .................. 564/216 X
3,919,269 11/1975 Jaffe et al. ....................... 564/218 X
3,960,886  6/1976 Schulenberg .................... 564/218 X Primary Examiner—Paul F. Shaver
Attorney, Agent, or Firm—Connolly and Hutz

[57]           ABSTRACT

Process for the preparation of pure 3-acetylaminoanilines of the general formula (1)

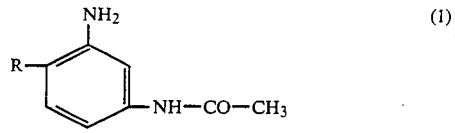

in which R denotes a hydrogen atom or an alkoxy group with 1–4 carbon atoms, by reduction of 1,3-dinitrobenzene in an alkanol with 1–4 carbon atoms to the 1,3-diaminobenzene or by reaction of 2,4-dinitrochlorobenzene with sodium hydroxide in an alkanol with 1–4 carbon atoms and subsequent reduction to the 2,4-diaminoalkoxybenzene, and in each case subsequent monoacetylation in the alkanol mentioned to give the 1-amino-3-acetylamino-benzene or the 2-amino-4-acetylamino-alkoxy-benzene and isolation of the compound of the above formula (1) obtained in the alkanolic solution, which optionally contains water, which comprises carrying out the isolation by precipitation of the compound of the above formula (1), in the form of the hydrohalide, from the alkanolic solution by means of hydrogen halide or aqueous hydrogen halide acid and subsequent filtration.

7 Claims, No Drawings

PROCESS FOR THE PREPARATION OF PURE 3-ACETYLAMINO-ANILINES

The present invention relates to a process for the preparation of pure 3-acetylamino-anilines of the general formula (1)

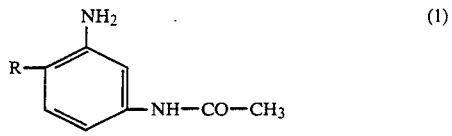

in which R denotes a hydrogen atom or an alkoxy group with 1–4 carbon atoms. Compounds of the above formula (1) are useful intermediates for a large number of industrially important disperse azo dyestuffs, in particular for the group of blue commercial dyestuffs of the C.I. Disperse Blue 79 type.

The compounds in question have hitherto been prepared industrially by acetylation of p-alkoxyanilines, nitration of the N-acetyl-p-alkoxyanilines thereby formed in the presence of solvents, and final reduction of the resulting 4-acetylamino-2-nitro-alkoxybenzenes or, if R is a hydrogen atom, partial sulfur reduction of 1,3-dinitrobenzene, acetylation of the resulting 3-nitroaniline and final hydrogenation.

Since these known preparation routes are very expensive, there has been no lack of attempts to obtain the required 3-acetylamino-anilines in another less expensive manner. A one-pot process in which 2,4-dinitrochlorobenzene is reacted with alkanols/sodium hydroxide to give 2,4-dinitroalkoxybenzenes, these are reduced to 2,4-diaminoalkoxybenzenes and the products are finally reacted with acetylating agents, preferably acetic anhydride, as selectively as possible to give 3-acetylamino-6-alkoxyanilines, is proposed in European Pat. No. 0,011,048 as the most advantageous synthesis of 3-acetylamino-6-alkoxyanilines. An analogous route (catalytic reduction of 1,3-dinitrobenzene in alkanols with subsequent monoacetylation which is as selective as possible) offers itself for 3-acetylamino-aniline (where R=H). Although these processes are considerably more economical, they do not lead to the purities of the target products of the general formula (1) which can be achieved by the first industrial routes mentioned. Purely selective monoacetylation of only one amino group in the 1,3-diaminobenzenes is not possible. The undesired bis-acetylamine is also formed in all cases, besides unreacted diamine. These secondary components (in an amount of in each case a few per cent in the most advantageous case in the process of European Pat. No. 0,011,048) cannot be removed in the working-up process proposed (removal of the alkanol by distillation, with subsequent crystallization from water). Whilst the 1,3-diaminobenzene (derivative) contained in the product for the most part decomposes, during working up, to black secondary products of unknown structure due to its high instability towards heat, the bis-acetylamine remains unchanged. The 3-acetylaminoanaline (derivative) isolated contains virtually all of both the black decomposition products of the diamine and the diacetylated secondary components, which means that only target products of considerably poorer quality are accessible by this economically advantageous route, in comparison with the industrial processes first mentioned, and these products cause technological problems during further processing to dyestuffs of the C.I. Disperse Blue 79 type and release the bis-acetylamine contained therein to the effluent in an undesirable manner.

There was therefore the object of rendering 3-acetylamino-anilines, which can be isolated with no impurities, industrially accessible, advantageously using an economically optimum one-pot process (for example in accordance with European Pat. No. 0,011,048). This object was achieved by the present invention in the following manner:

It was found that 3-acetylamino-anilines of the above-mentioned general formula (1) can be prepared in the pure form by monoacetylating the 1,3-diaminobenzene obtained in a known manner by reduction of 1,3-dinitrobenzene in an alkanol with 1–4 carbon atoms, or the 2,4-diaminoalkoxybenzene obtained in a known manner by reaction of 2,4-dinitrochlorobenzene with sodium hydroxide in an alkanol with 1–4 carbon atoms and subsequent reduction, preferably with acetic anhydride in a known manner in the alkanol mentioned to give the 1-amino-3-acetylaminobenzene or the 2-amino-4-acetylamino-alkoxy-benzene, and precipitating the compound of the above general formula (1) obtained in the alkanolic solution, which may contain water, selectively and virtually quantitatively by means of hydrogen halide in the form of the corresponding hydrohalide and separating it off by filtration.

In this process, all the concomitant substances (diaminobenzenes and/or their decomposition products as well as bis-acetylamines) remain entirely in solution and can be removed by filtration.

The process according to the invention is extremely surprising inasmuch as, according to present knowledge, aromatic amines, especially anilines substituted by amino, alkoxy and/or acetylamino groups, are capable of forming hydrohalides readily soluble in water and alcohols, and, if they form sparingly soluble salts at all, then these are at best sparingly soluble sulfates. Thus, certain toluidines, chloroanilines and anisidines, for example 2,4-diamino-toluene, -chlorobenzene, -anisole and -phenetole, which are industrially important intermediates for hair dyes and fur dyes, are generally isolated from alcoholic solution as sparingly soluble sulfates, since the corresponding hydrohalides are readily soluble (cf. for example, Monatshefte für Chemie 22, 119; and Recueil des trav. chim. des Pays Bas 47, 185).

In contrast, 3-acetylamino-6-alkoxyanilines in which the alkoxy radical contains more than one 0 atom (such as, for example, the β-methoxyethoxy radical) and/or the acylamino group contains more than 2 carbon atoms (such as, for example, the propionylamino or butyroylamino group), and 6-acylamino-4-amino-1,3-xylenes form neither sparingly soluble sulfates nor sparingly soluble hydrohalides in alcohols.

It was therefore neither to be predicted nor to be assumed from the present state of knowledge that 3-acetylamino-anilines of the general formula (1) form extremely sparingly soluble hydrohalides in low molecular weight alkanols, which may contain water, and can be separated off as such by filtration from all the impurities which are not capable of forming these salts (diaminobenzenes and bis-acetylamines).

This applies all the more, since one of the compounds which can be precipitated according to the invention, that is to say 3-acetylamino-aniline hydrochloride, is even claimed in the literature to have a good solubility in methanol (JACS 39, 1948).

The lower alkanols which are at least partly miscible with water, such as methanol, ethanol, n- and isopropanol and the isomeric butanols, may be mentioned as alkanols which can be used according to the invention. In the case of the alkoxy derivatives which can be precipitated according to the invention, alkanols which are of particular advantage are of course those which are used in excess for the replacement of chlorine in the one-pot process described in European Pat. No. 0,011,048 and are used as solvents in the subsequent stages (reduction and acetylation), since in these cases the one-pot reaction can be directly followed, without intermediate isolation of the crude 3-acetylamino-6-alkoxy-anilines, by isolation of the desired hydrohalides of the target products containing no by-products.

Since the hydrohalides which can be precipitated according to the invention are also sparingly soluble in water-containing alkanols, the salt formation can be effected either by passing at least the stoichiometric amount of gaseous hydrogen halide, such as, for example, hydrogen bromide, or, preferably, hydrogen chloride, into the alcoholic solution of the compound of the general formula (1), which optionally contains water, or, particularly advantageously, by adding at least the stoichiometric amount of aqueous hydrogen halide acid, for example aqueous hydrobromic acid or, preferably, hydrochloric acid, to this solution.

According to the invention, the water contents which can be tolerated, without a reduction in yield, in the alkanols used as the precipitating medium are up to 30% by weight, or up to the saturation limit in the case of alkanols which have only a limited water-miscibility.

Suitable precipitating agents are gaseous hydrogen halides or their aqueous solutions, up to concentrations which allow the abovementioned water contents of the precipitating medium to be maintained. In principle, all of the hydrogen halides can be used. For economic reasons, hydrogen chloride and hydrogen bromide, in particular hydrogen chloride, are preferred.

The precipitation of the hydrohalides of the 3-acetylamino-anilines of the general formula (1) can be carried out in wide temperature ranges. The upper limit is the boiling point of the precipitating medium. Temperatures from 20° to 50° C. are preferred, since partial hydrolysis of the acetylamino group cannot always be excluded at a higher temperature and over a long residence time.

The precipitated 3-acetylamino-aniline hydrohalides are advantageously isolated at low temperatures, for example at 0° to 20° C., since, as expected, the solubility of the hydrohalides increases at elevated temperatures, although to a surprisingly small extent, and losses in yield must therefore be accepted at higher isolation temperatures.

At least the stoichiometric amount of the hydrogen halide employed for the precipitation is used. An excess is not harmful, since the hydrohalides of the concomitant substances are readily soluble in the precipitating medium, but an excess in certain circumstances affects the profitability of the purification process.

Virtually sole precipitation of the 3-acetylamino-aniline hydrohalide of the above general formula (1) is also effected if the precipitation solution contains alkali metal or alkaline earth metal salts, for example magnesium acetate, as is preferred in the process of European Pat. No. 0,011,048. This is particularly the case if aqueous hydrogen halide acids are used for the precipitation, since an aqueous alcoholic precipitation medium results, in which the alkali metal or alkaline earth metal halides which may be formed in some cases for the most part remain dissolved. Salts which are undissolved to a small extent and are thus isolated with the target products do not interfere in subsequent reactions and can therefore be tolerated, since they can be removed without problems in the course of the dyestuff synthesis.

The process according to the invention is to be considered as novel and surprising. This is all the more the case since the target products are in no case capable of forming sparingly soluble sulfates in alkanols and in this respect already differ from the related above-mentioned aniline derivatives. It was neither obvious nor predictable that, with this state of affairs, the hydrohalides, which are otherwise generally considerably more readily soluble, are suitable for virtually quantitative precipitation of the 3-acetylamino-anilines dissolved in alkanols and can be separated off by filtration from secondary components which remain in solution.

The process according to the invention enables the industrially important 3-acetylamino-anilines of the general formula (1) to be prepared in the form of their hydrohalides by an economically optimum route, starting from 2,4-dinitrochlorobenzene or 1,3-dinitrobenzene, in a one-pot reaction in a purity such as has hitherto been possible to achieve only by the considerably more expensive routes via nitration of 4-acetylamino-alkoxybenzenes or via acetylation of 3-nitroaniline. In addition, the impurities separated off are obtained as a concentrated bottom product of the distillation, after regeneration of the alcohols, and this product can advantageously be disposed of by combustion, leading to a significant reduction in the load on the effluent. The process according to the invention thus represents a considerable industrial advance compared with the prior art.

It is of course also possible for the compounds of the general formula (1) to be prepared by any desired other route, before their precipitation according to the invention and removal from the optionally alkanolic solution by filtration, and to isolate them with the impurities obtained, to dissolve the products intermediately isolated in an alkanol with 1-4 carbon atoms and then to isolate them according to the invention in the form of the hydrohalides. However, it is expedient and also advantageous to convert the starting compounds, i.e. 1,3-dinitrobenzene or 2,4-dinitrochlorobenzene, into the compounds of the above formula (1) in the stated manner which is known per se in the course of the economically optimum one-pot reaction, in which case these compounds of the formula (1) are already obtained as a solution in the optionally water-containing alkanols, because of the use of alkanols with 1-4 carbon atoms in the preceding reaction stages, and can be isolated therefrom according to the invention.

The pure 3-acetylamino-aniline hydrohalides accessible in this way can in most cases be used as such for subsequent reactions. If necessary, there are no problems in preparing the free pure 3-acetylamino-anilines from these products by neutralizati on by means of alkalis, for example in aqueous solution or suspension, and, if appropriate, separating off these pure products from the resulting aqueous alkali metal halide solutions by filtration.

The following examples are intended to illustrate the invention in more detail, without limiting it to the embodiments described therein.

EXAMPLE 1

197 parts of 37% strength hydrochloric acid are added dropwise, at 20°–25° C. in the course of 30 minutes, with stirring, to a dark solution, obtained according to Example 1 of European Pat. No. 0,011,048 by reaction of 213 parts of 2,4-dinitrochlorobenzene with 42 parts of sodium hydroxide in 632 parts of methanol, subsequent hydrogenation on Pd/charcoal at 60° C. and then acetylation with 98 parts of acetic anhydride in the presence of 22 parts of magnesium oxide at 0°–5° C., of 6-methoxy-3-acetylamino-aniline which, according to "high performance liquid chromatography analysis" ("HPLC analysis") contains 8.9 parts of 2,4-bis-acetylaminoanisole and 3.5 parts of 2,4-diaminoanisole, as well as black decomposition products formed by oxidation, in addition to 153 parts of the target product. The mixture is subsequently stirred for 1 hour and cooled to 0°–5° C. and the 6-methoxy-3-acetylamino-aniline hydrochloride precipitated is isolated by filtration. The product is washed twice with 100 parts of methanol to give, after drying in vacuo, 188.5 parts of 6-methoxy-3-acetylamino-aniline hydrochloride, which, besides about 5% of magnesium chloride, contains no organic by-products detectable by thin-layer chromatography ("TLC") or HPLC analysis. The product isolated thus corresponds to 179.1 parts of 100% pure 6-methoxy-3-acetylamino-aniline hydrochloride, which corresponds to a yield of 82.7% of theory, based on the 2,4-dinitrochlorobenzene employed.

A salt-free pure product (content of 6-methoxy-3-acetylamino-aniline according to HPLC analysis: 99%) is obtained in a yield of 80.2% of theory (173.6 parts) by washing the methanol-moist filter cake twice with in each case 100 parts of ice-water and subsequent drying in vacuo.

EXAMPLE 2

194 parts of dried crude 6-ethoxy-3-acetylaminoaniline (containing, besides 175.5 parts of target product, 9.5 parts of 2,4-bis-acetylaminophenetole and 3.5 parts of 2,4-diaminophenetole, in addition to dark impurities formed by oxidation) obtained according to Example 3 of European Pat. No. 0,011,048, are dissolved in 250 parts of ethanol at 50° C., with stirring. After cooling to 20°–30° C., the dark solution is gassed with about 35–40 parts of hydrogen chloride gas in the course of 1 hour and is subsequently stirred for 1 hour, and the 6-ethoxy-b 3-acetylamino-aniline hydrochloride precipitated is isolated, after cooling to 0°–5° C., by filtration on a suction filter. The product is washed twice with 75 parts of ethanol each time and dried in vacuo to give 204.0 parts of 6-ethoxy-3-acetylamino-aniline hydrochloride (no impurities detectable by HPLC analysis, purity content by diazotization: 99.2%), which corresponds to a yield of 88.5% of theory (based on the crude product employed) or 97.8% of theory (based on the target product contained therein).

If 150 parts of methanol are used instead of 250 parts of ethanol and the procedure is otherwise as described above, 202.8 parts of 6-ethoxy-3-acetylamino-aniline hydrochloride of the same quality are obtained (yield: 88.0% of theory, based on the crude product, or 97.2% of theory, based on the target product contained therein).

EXAMPLE 3

A solution of 168 parts of 1,3-dinitrobenzene in 400 parts of methanol is transferred to a 1 liter autoclave together with 4 parts of 5% strength Pd/charcoal catalyst. After flushing with nitrogen and then with hydrogen, hydrogenation is carried out at 40°–65° C./20 bar of hydrogen. When no further hydrogen is taken up, the mixture is cooled to room temperature, let down and clarified from the catalyst.

22 parts of magnesium oxide are added to the resulting aqueous-methanolic solution of m-phenylenediamine, the mixture is cooled to 0°–5° C. and acetylation is then carried out by dropwise addition of 100 parts of acetic anhydride in the course of 2 hours. A dark solution results which, according to HPLC analysis, contains, in addition to 133.5 parts of 3-acetylamino-aniline, 9.4 parts of 1,3-bis-acetylaminobenzene, 1.9 parts of m-phenylenediamine and black impurities formed by oxidative decomposition.

150 parts of 30% strength hydrochloric acid are added dropwise to this solution at 10°–15° C. in the course of 30 minutes, the mixture is subsequently stirred for 30 minutes and cooled to 0° to 5° C. and the 3-acetylamino-aniline hydrochloride precipitated is filtered off. The filter cake is washed twice with 75 parts of methanol each time and dried in vacuo. 165 parts of solid are obtained which, besides about 4% of magnesium salts, contains no organic by-products detectable by TLC or HPLC analysis and, as a result of diazotization, shows a purity of 96.0% ( 158.4 parts of 3-acetylamino-aniline hydrochloride), which corresponds to a yield of 84.9% of theory, based on 1,3-dinitrobenzene.

A salt-free product with a diazotization value of 99.4% (155.2 parts, corresponding to 83.2% of theory) is obtained by washing the methanol-moist filter cake twice with 60 parts of ice-water each time.

If 500 parts of isopropanol are used instead of the 400 parts of methanol and the procedure is otherwise as described above, the 3-acetylamino-aniline hydrochloride is obtained in comparable yield and quality.

EXAMPLE 4

208 parts of dried crude 6-n-propoxy-3-acetylamino-aniline obtained according to Example 7 of European Pat. No. 0,011,048 (containing, in addition to 190.3 parts of target product, 8.8 parts of 2,4-bis-acetylamino-1-n-propoxybenzene and 3.5 parts of 2,4-diamino-1-n-propoxybenzene, as well as small amounts of magnesium acetate and oxidative decomposition products) are dissolved in 300 parts of ethanol at 50° C., with stirring, and, after the solution has been cooled to 25° C., 170 parts of 48% strength hydrobromic acid are added dropwise in the course of 1.5 hours. The precipitate which has separated out is filtered off with suction at 0°–5° C., washed with two portions of 60 parts of ethanol and dried in vacuo. 257.1 parts of 6-n-propoxy-3-acetylamino-aniline hydrobromide (no impurities detectable by HPLC, purity by diazotization: 99.4%) are obtained, which corresponds to a yield of 88.9% of theory (based on the crude feed product) or 97.2% of theory (based on the target product contained therein).

If 350 parts of isobutanol are used instead of 300 parts of ethanol and the procedure is otherwise as described above, 6-n-propoxy-3-acetylamino-aniline hydrobromide is obtained in comparable quality with a yield about 2% lower.

EXAMPLE 5

180 parts of a black crude 6-methoxy-3-acetylamino-aniline (prepared by the procedure of European Pat. No. 0,011,048, but with the addition of 10% of water before the hydrogenation and with an increase in the acetylation temperature to 20°-25° C., which resulted in less smooth reduction of the nitro groups and significantly lower selectivity in the monoacetylation), which, according to HPLC, contained, in addition to 124 parts of target product and 22 parts of 2,4-bisacetylamino-anisole, considerable amounts (about 30-35 parts) of unidentifiable byproducts and decomposition products formed by oxidation, were dissolved in 500 parts of methanol at 50° C. and, after the solution had been cooled to 20°-25° C., 100 parts of 30% strength hydrochloric acid were added dropwise in the course of 30 minutes, with stirring, and the mixture was then subsequently stirred for 1.5 hours. The product isolated by filtration on a suction filter after the mixture had been cooled to 0°-5° C. was washed twice with 100 parts of methanol each time and dried in vacuo. 144 parts of almost colorless 6-methoxy-3-acetylamino-aniline hydrochloride were obtained which, according to HPLC analysis, contained no organic impurities at all and had a purity, by diazotization, of 99.3%, corresponding to a yield of 96.8% of theory, based on 6-methoxy-3-acetylamino-aniline contained in the crude product.

The free 6-methoxy-3-amino-aniline can be obtained in a yield of 92.8% of theory, based on the target product contained in the crude product, by stirring the methanolic filter cake with cold water for 1 hour, dropwise addition of 33% strength sodium hydroxide solution to pH 7.5 and cooling of the resulting suspension to 0°-5° C., followed by filtration, washing twice with 50 parts of ice-water each time and drying in vacuo.

EXAMPLE 6

The dark butanolic solution, obtained according to European Pat. No. 0,011,048 by reaction of 213 parts of 2,4-dinitrochlorobenzene with 632 parts of n-butanol and 42 parts of sodium hydroxide, after hydrogenation and acetylation, of 6-n-butoxy-3-acetylamino-aniline which, according to HPLC analysis, contains, in addition to 195 parts of target product, 11.9 parts of 2,4-bis-acetylamino-1-n-butoxy-benzene and 8.1 parts of 2,4-diamino-1-n-butoxybenzene, in addition to unknown decomposition products formed by oxidation, is precipitated by gassing with 35-40 parts of hydrogen chloride at 20°-30° C. for one hour and, after cooling to 0°-5° C., the precipitate is filtered off with suction, washed twice with 50 parts of methanol each time and dried in vacuo. 221.2 parts of 6-n-butoxy-3-acetylamino-aniline hydrochloride are obtained which, besides about 3% of magnesium chloride, contains no impurities at all which can be detected by HPLC analysis (purity by diazotization: 95.8%). This corresponds to a yield of 214.1 parts of 100% pure 6-n-butoxy-3-acetylamino-aniline hydrochloride (82.8% of theory, based on 2,4-dinitrochlorobenzene).

EXAMPLE 7 (comparison example)

If 30% strength hydrochloric acid is added to a methanolic solution, obtained according to Example 4 of European Pat. No. 0,011,048, of 6-methoxy-3-propionylaminoaniline, no precipitation at all occurs. Any by-products cannot be removed by this route.

The same negative result is obtained if gaseous hydrogen chloride or hydrogen chloride dissolved in water is added to an alcoholic solution of 6- -methoxyethoxy-3-acetylamino-aniline (compound 8 from European Pat. No. 0,011,048) or of 6- -hydroxyethoxy-3-acetylamino-aniline (compound 15 from European Pat. No. 0,011,048).

We claim:

1. A process for the preparation of a pure 3-acetylamino-aniline of the formula (1)

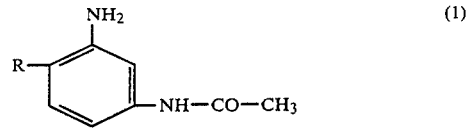

in which R denotes a hydrogen atom or an alkoxy group with 1-4 carbon atoms, by reduction of 1,3-dinitrobenzene in an alkanol with 1-4 carbon atoms to 1,3-diaminobenzene or by reaction of 2,4-dinitrochlorobenzene with sodium hydroxide in an alkanol with 1-4 carbon atoms and subsequent reduction to the 2,4-diaminoalkoxybenzene, and in each case subsequent monoacetylation in the alkanol mentioned to give the 1-amino-3-acetylamino-benzene or the 2-amino-4-acetylamino-alkoxy-benzene and isolation of the compound of the above formula (1) obtained in the alkanolic solution, which optionally contains water, which comprises carrying out the isolation by precipitation of the compound of the above formula (1), in the form of the hydrohalide, from the alkanolic solution by means of hydrogen halide or aqueous hydrogen halide acid and subsequent filtration.

2. The process as claimed in claim 1, wherein the precipitation of the compound of the formula (1) is carried out by passing at least the stoichiometric amount of gaseous hydrogen halide, preferably hydrogen chloride, into the alkanolic solution, which optionally contains water.

3. The process as claimed in claim 1, wherein the precipitation of the compound of the formula (1) is carried out by adding at least the stoichiometric amount of aqueous hydrogen halide acid, preferably hydrochloric acid, to the alkanolic solution, which optionally contains water.

4. The process as claimed in claim 1, wherein the water content of the alkanols used as the solvent and precipitating medium is up to 30% by weight.

5. The process as claimed in claim 1, wherein the water content of the alkanols which are used as the solvent and precipitating medium and have only a limited water-miscibility is up to the saturation limit.

6. The process as claimed in claim 1, wherein the precipitation of the compound of the formula (1) in the form of the hydrohalide is carried out at a temperature which is no higher than the boiling point of the precipitating medium.

7. The process as claimed in claim 1, wherein the precipitation of the compound of the formula (1) in the form of the hydrohalide is carried out at a temperature of 20°-50° C.

* * * * *